United States Patent [19]
Kaiser

[11] Patent Number: 5,363,864
[45] Date of Patent: Nov. 15, 1994

[54] SURGICAL METHOD USING FINGER PROTECTING SHEATH

[75] Inventor: Larry R. Kaiser, Wynnewood, Pa.

[73] Assignee: The Trustees of the University of Pennsylvania, University of Pa.-Center for Technology Transfer, Philadelphia, Pa.

[21] Appl. No.: 53,949

[22] Filed: Apr. 27, 1993

[51] Int. Cl.⁵ .............................................. A61B 19/00
[52] U.S. Cl. .................................................... 128/898
[58] Field of Search .............................. 128/897–899, 128/749, 751; 602/22, 61; 63/15, 15.8

[56] References Cited

U.S. PATENT DOCUMENTS

| | | | |
|---|---|---|---|
| 4,640,273 | 2/1987 | Greene et al. | 128/3 |
| 5,257,637 | 11/1993 | El Gazayerli | 128/898 |
| 5,281,234 | 1/1994 | Wilk et al. | 128/898 |

Primary Examiner—Lee S. Cohen
Assistant Examiner—John P. Lacyk
Attorney, Agent, or Firm—Howson and Howson

[57] ABSTRACT

In thoracoscopic surgery digital palpation of intrathoracic anatomical structures is facilitated by the use of a rigid finger sheath which prevents the forces exerted by the patients ribs from causing numbness in the surgeon's finger. The finger sheath has an enlarged end which prevents it from falling into the patient's thoracic cavity.

3 Claims, 1 Drawing Sheet

SURGICAL METHOD USING FINGER PROTECTING SHEATH

BRIEF SUMMARY OF THE INVENTION

This invention pertains to thoracoscopic surgery, and in particular to a ring or sheath adapted for use on a surgeon's finger in order to permit the surgeon to palpate anatomical structures or lesions within a patient's rib cage without causing the finger to be squeezed by the patient's ribs.

Ordinarily, in thoracoscopic surgery trocar/cannula combinations are inserted through the patient's chest wall. After insertion of each trocar/cannula combination, the trocar is withdrawn and the cannula is left in place to provide access to the thoracic cavity. Fiberoptic illumination and image-conducting instruments are typically inserted through one cannula while instruments such as forceps, scissors, dissecting spatulas, etc. are inserted through other cannulae. In some surgical procedures, a gas is fed in through still another cannula to induce pneumothorax.

More recently, it has been discovered that some of these trocar/cannula combinations can be eliminated. Specially designed instruments, for example, forceps having a length of approximately 12 to 13 inches and having their hinges located approximately 5.5 inches from the proximal end can be inserted directly through incisions made in the patient's chest without the need for a cannula. The elimination of one or more trocar/cannula combinations reduces the cost of the surgery, and increases the ability of the surgeon to reach and operate on various structures within the thoracic cavity.

Another advantage resulting from the elimination of certain cannulae is that the surgeon is able to insert his fingers through the incisions, in between the patient's ribs, in order to palpate anatomical structures or lesions within the thoracic cavity.

The advantage of using these incisions for digital palpation in order to determine the condition of the patient is readily apparent. However, because of the anatomical nature of the rib cage, the patient's bones, muscles and tendons combine to exert pressure on the surgeon's finger, thereby numbing the finger within a short period of time and rendering it virtually useless to enable the surgeon to determine the condition of the anatomical structure, tumors or lesions within.

The principal object of the invention is to provide protection to the surgeon's finger in order to permit effective palpation of the thoracic cavity. The finger sheath of this invention is simple to manufacture and is reliable, safe, effective and easy to use during surgery.

The finger sheath according to this invention is a rigid tube, preferably of stainless steel, having a length of approximately 25 to 35 mm and an internal diameter ranging from 20 to 25 mm. The circular edges of the openings of both ends of the ring are rounded. One end of the ring is enlarged radially to prevent it from slipping into the thoracic cavity.

Further objects and advantages of the invention will be apparent from the following detailed description when read in conjunction with the drawings.

DETAILED DESCRIPTION

Figure 1:
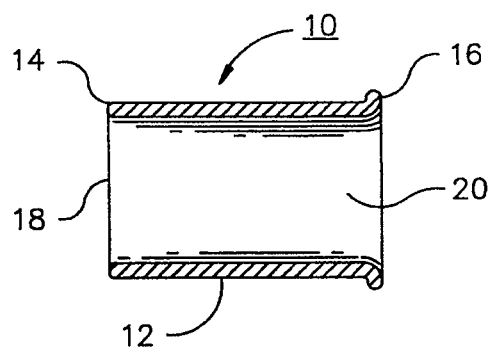
FIG. 1 depicts a finger sheath in accordance with the invention in axial cross-section.
Figure 2:
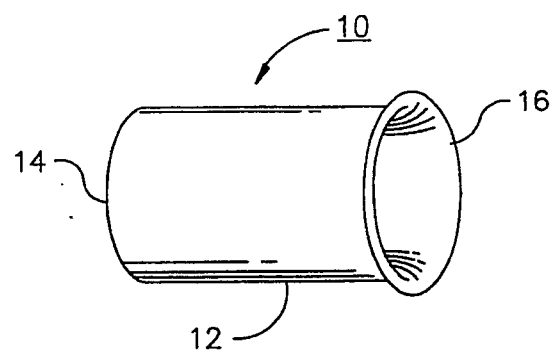
FIG. 2 depicts a finger sheath in perspective view.

As shown in FIGS. 1 and 2, the finger sheath 10 in accordance with the invention comprises a rigid tube 12, of circular cross-section, having an axial length in the range of approximately 25 to 35 mm, and an internal diameter in the range of approximately 20 to 25 mm. The tube is preferably machined from 300 series stainless steel. The wall thickness of the tube is preferably in the range of approximately 0.71 to 0.77 mm. The circular edges 14 and 16 of the openings 18 and 20 of both ends of the rings are rounded. The end of the tube having opening 20 is enlarged radially both internally and externally so that it can easily receive the surgeon's finger, and so that it will not slide into the patient's thoracic cavity.

The ring is formed from a blank in the form of a tube of stainless steel having a wall thickness equal to the radial distance from a cylinder conforming to the inner wall of ring to the outer periphery of the enlarged end. The blank is turned on a lathe to remove the outer surface of the tube along a major portion of its length and to form the outer surface of the enlarged end. The inner surface of the enlarged end is then formed by turning, using an appropriate cutting tool. The ring is then cut off from the tube and polished to smooth the outer surface and to round and smooth the ends of the tube.

Figure 3:
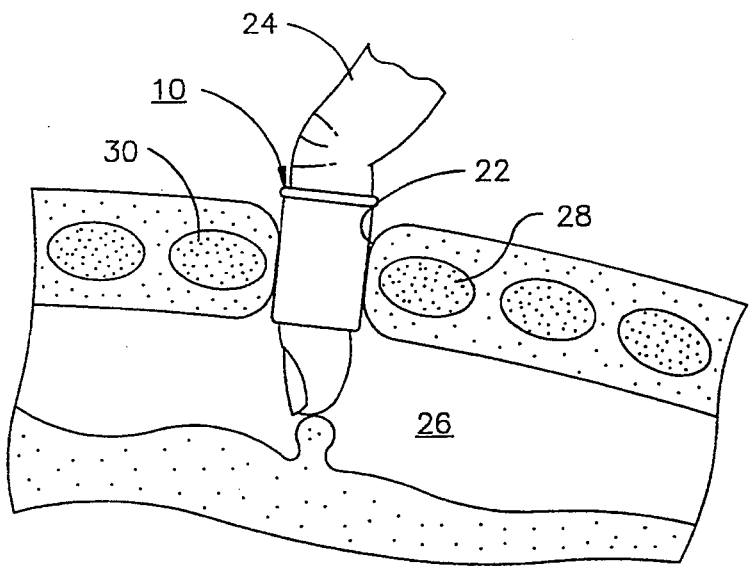
FIG. 3 is a cross-sectional view showing the finger sheath located on the surgeon's finger and between two ribs of a patient.

During surgery, as shown in FIG. 3, a small incision 22 is made in the patient's chest wall primarily in order to permit the insertion of an elongated thoracoscopy forceps. The forceps is described in my co-pending U.S. patent application entitled TISSUE GRASPING FORCEPS FOR USE IN THORACOSCOPIC SURGERY, filed simultaneously herewith, and incorporated herein by reference. The surgeon can place the finger ring 10 of the invention on a finger 24, and insert his sheathed finger into the thoracic cavity 26 by passing it between two ribs 28 and 30. The surgeon can then palpate anatomical structures, tumors or lesions within the thoracic cavity, without feeling pressure from the ribs squeezing on his finger.

Figure 4:
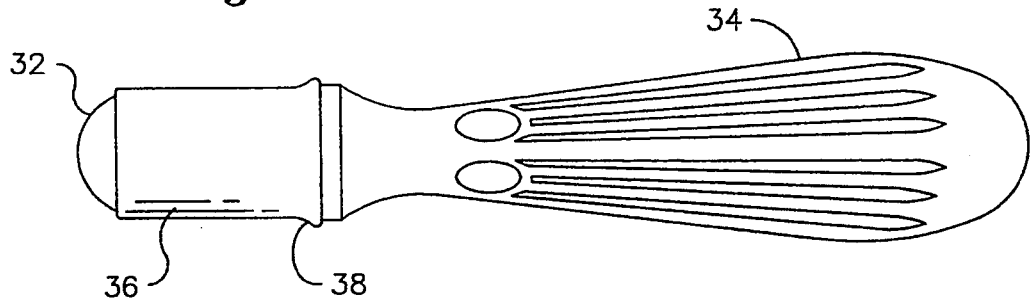
FIG. 4 is an elevational view showing a finger sheath with an obturator.

In an alternative method, the surgeon can utilize an obturator to insert the ring. As shown in FIG. 4, an obturator having a rounded end 32 and a handle 34, is inserted through ring 36 from the enlarged end 38 so that the rounded end of the obturator projects from the opposite end of the ring. The obturator aids the insertion of the ring into the space between the ribs of the patient. After insertion of the ring, the obturator is withdrawn, and the surgeon can insert a finger through the ring to palpate internal anatomical structures in the manner depicted in FIG. 3.

Various modifications can be made to the ring. For example, the ring can be made with an oval cross-section rather than a circular cross-section. The enlargement at the enlarged end can be in the form of a bead, as shown, or alternatively it can be in the form of a gradual flare. The enlargement can be formed by a turning process in which metal is cut away from the exterior of the remainder of a blank tube, or, alternatively, by the use of a suitable flaring tool to enlarge the opening at one end of the blank tube without cutting away metal. The ring can be made in various diameters to accommodate different finger sizes, and its length can be varied as well. These and other modifications which will occur to persons skilled in the art, can be made without departing from the scope of the invention as defined in the following claims.

I claim:

1. A method of thoracoscopic surgery comprising:
   forming an incision in the chest wall of a patient between two adjacent ribs; and
   palpating, with a finger, an anatomical structure within the patient's thoracic cavity, with a rigid tube surrounding the finger and located between said two adjacent ribs;
   whereby pressure exerted by said ribs is exerted on the rigid tube instead of on the surgeon's finger.

2. The method according to claim 1 including placing the tube on the finger, and inserting the finger, with the tube fitted on it, into said incision until the tube is located between said two adjacent ribs.

3. The method according to claim 1 including inserting an obturator through the tube; inserting the obturator, with the tube fitted on it, into said incision until the tube is located between said two adjacent ribs; withdrawing the obturator; and, after withdrawal of the obturator, with the tube in place between said two adjacent ribs, inserting the finger through said tube.

* * * * *